(12) United States Patent
Matta et al.

(10) Patent No.: US 9,278,955 B2
(45) Date of Patent: Mar. 8, 2016

(54) ASCORBIC ACID SALT OF SUNITINIB

(71) Applicant: RANBAXY LABORATORIES LIMITED, New Delhi, Delhi (IN)

(72) Inventors: Hari Babu Matta, Prakasam (IN); Mahavir Singh Khanna, New Delhi (IN); Mohan Prasad, Gurgaon (IN)

(73) Assignee: SUN PHARMACEUTICAL INDUSTRIES LIMITED, Mumbai (IN)

( * ) Notice: Subject to any disclaimer, the term of this patent is extended or adjusted under 35 U.S.C. 154(b) by 0 days.

(21) Appl. No.: 14/147,766

(22) Filed: Jan. 6, 2014

(65) Prior Publication Data

US 2015/0111940 A1    Apr. 23, 2015

(30) Foreign Application Priority Data

Oct. 18, 2013    (IN) .......................... 3113/DEL/2013

(51) Int. Cl.
| | | |
|---|---|---|
| *A61K 31/40* | (2006.01) | |
| *C07D 403/06* | (2006.01) | |
| *C07D 307/58* | (2006.01) | |
| *A61K 31/404* | (2006.01) | |

(52) U.S. Cl.
CPC ............ *C07D 403/06* (2013.01); *A61K 31/404* (2013.01); *C07D 307/58* (2013.01)

(58) Field of Classification Search
CPC .. C07D 403/06; C07D 307/58; C07D 209/34; A61K 31/404; A61K 31/4015; C07C 59/245

USPC .................................. 514/414, 418; 548/468
See application file for complete search history.

(56) References Cited

U.S. PATENT DOCUMENTS

| | | | |
|---|---|---|---|
| 6,573,293 B2 | 6/2003 | Tang et al. ..................... | 514/414 |
| 7,125,905 B2 | 10/2006 | Tang et al. ..................... | 514/414 |
| 7,435,832 B2 * | 10/2008 | Hawley et al. ................. | 548/465 |
| 8,466,190 B2 * | 6/2013 | Konduri et al. ................ | 514/414 |
| 8,686,023 B2 * | 4/2014 | Selic ............................. | 514/414 |
| 2003/0069298 A1 | 4/2003 | Hawley et al. ................. | 514/414 |
| 2007/0191458 A1 | 8/2007 | Hawley et al. ................. | 514/414 |
| 2011/0263671 A1 * | 10/2011 | Selic ............................. | 514/418 |
| 2015/0112085 A1 * | 4/2015 | Matta et al. .................... | 548/468 |

FOREIGN PATENT DOCUMENTS

| | | | | |
|---|---|---|---|---|
| CA | 2 741 606 | 5/2010 | .......... | C07D 403/06 |
| WO | WO 03/016305 | 2/2003 | .......... | C07D 403/06 |
| WO | WO 2009/104021 | 8/2009 | .......... | C07D 403/06 |
| WO | WO 2010/081443 | 7/2010 | .............. | A61K 9/14 |
| WO | WO 2011/033472 | 3/2011 | .......... | C07D 403/06 |
| WO | WO 2011/061613 | 5/2011 | .......... | C07D 403/06 |

OTHER PUBLICATIONS

Berge et al., "Pharmaceutical Salts", *Journal of Pharmaceutical Sciences*, 66(1):1-19 (1977).

* cited by examiner

*Primary Examiner* — My-Chau T Tran

(57) ABSTRACT

The present invention relates to an ascorbic acid salt of sunitinib and a process for its preparation. The present invention further provides a crystalline Form I of an L-ascorbic acid salt of sunitinib.

18 Claims, 3 Drawing Sheets

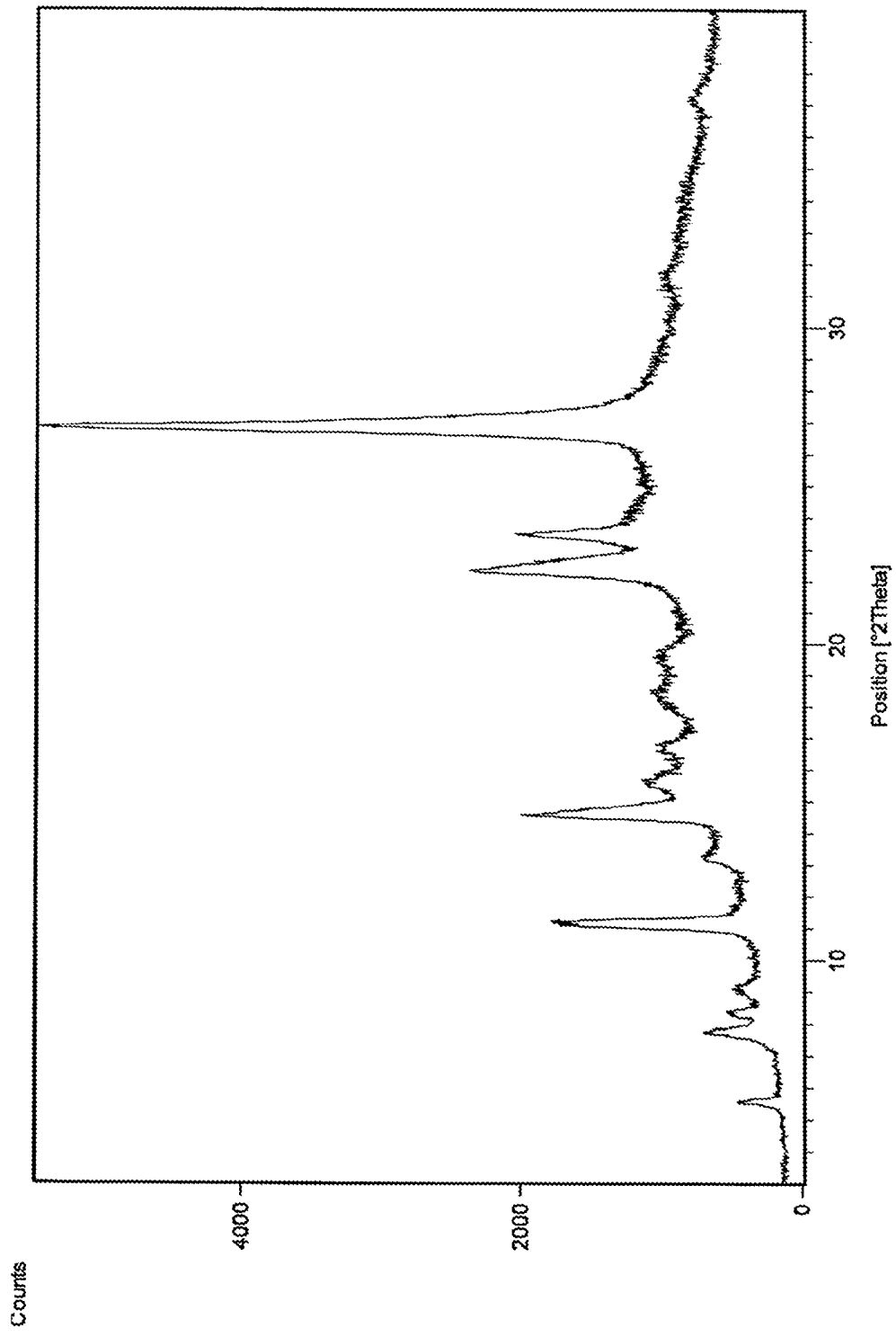
FIGURE 1: XRPD PATTERN OF THE CRYSTALLINE FORM OF ASCORBIC ACID SALT OF SUNITINIB PREPARED ACCORDING TO EXAMPLE 1.

FIGURE 1A: TABLE OF VALUES FOR THE XRPD PATTERN DEPICTED IN FIGURE 1.

| Pos [°2 Th] | d-spacing [Å] | Rel. Int. [%] |
|---|---|---|
| 5.53 | 15.97 | 6.08 |
| 7.71 | 11.47 | 10.57 |
| 8.39 | 10.53 | 5.90 |
| 9.16 | 9.65 | 3.87 |
| 11.06 | 8.00 | 27.79 |
| 11.28 | 7.84 | 21.83 |
| 13.21 | 6.70 | 4.74 |
| 14.58 | 6.08 | 32.29 |
| 15.60 | 5.68 | 11.52 |
| 16.69 | 5.31 | 7.46 |
| 18.50 | 4.80 | 6.20 |
| 19.63 | 4.52 | 4.50 |
| 22.28 | 3.99 | 33.18 |
| 23.45 | 3.79 | 22.63 |
| 26.79 | 3.33 | 100.00 |
| 31.67 | 2.82 | 1.94 |
| 37.12 | 2.42 | 1.84 |

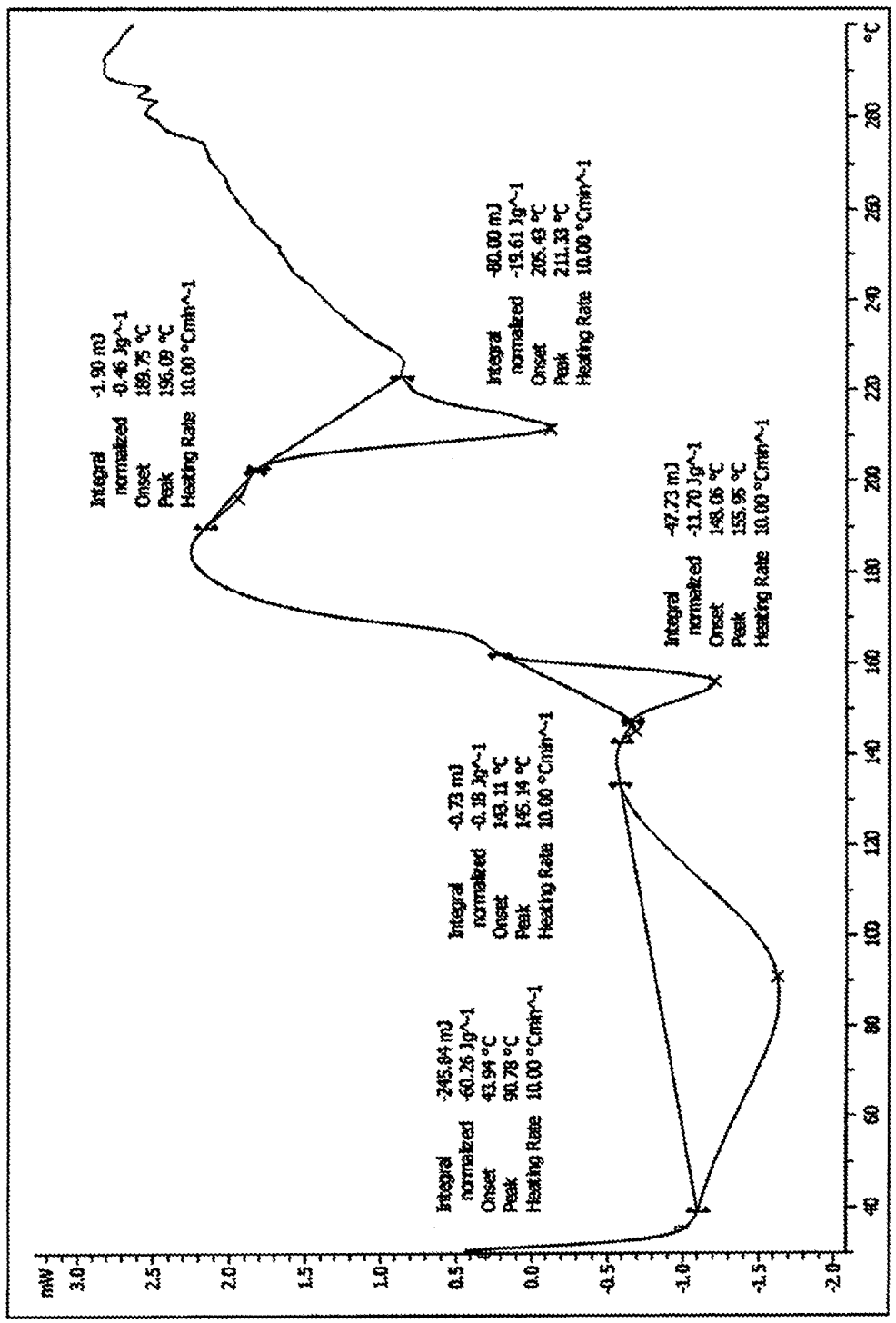
FIGURE 2: DSC PATTERN OF THE CRYSTALLINE FORM I OF ASCORBIC ACID SALT OF SUNITINIB PREPARED ACCORDING TO EXAMPLE 1.

ASCORBIC ACID SALT OF SUNITINIB

FIELD OF THE INVENTION

The present invention relates to an ascorbic acid salt of sunitinib and a process for its preparation. The present invention further provides a crystalline Form I of an L-ascorbic acid salt of sunitinib.

BACKGROUND OF THE INVENTION

Sunitinib is chemically described as N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide and is represented by Formula I.

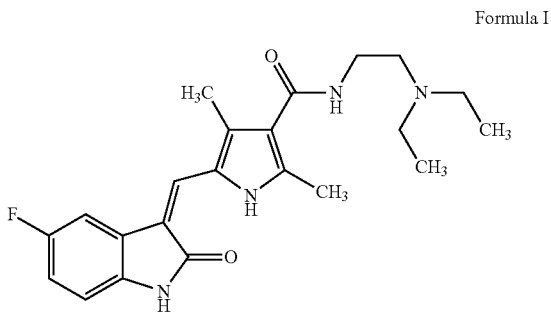 [SMILES: CCN(CC)CCNC(=O)c1c(C)[nH]c(/C=C2\C(=O)Nc3ccc(F)cc32)c1C]

Formula I

Sunitinib is an oral multi-kinase inhibitor and is useful for the treatment of gastrointestinal stromal tumors and advanced renal cell carcinoma. Sunitinib is commercially available as an L-malate salt, which is described chemically as butanedioic acid, hydroxy-, (2S)-, compound with N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide (1:1).

U.S. Publication Nos. 2003/0069298 and 2007/0191458 disclose crystal Forms I and II of an L-malic acid salt of sunitinib. PCT Publication No. WO 2009/104021 discloses that crystalline Form II of an L-malic acid salt of sunitinib is hygroscopic, thermodynamically unstable, and appears to readily convert to Form I.

PCT Publication No. WO 2011/061613 discloses a stable crystalline Form II of an L-malic acid salt of sunitinib and a process for its preparation. The publication further discloses that stable crystalline Form II does not convert to any other form or absorb moisture on storage.

SUMMARY OF THE INVENTION

The present invention relates to an ascorbic acid salt of sunitinib and a process for its preparation. The present invention further provides a crystalline Form I of an L-ascorbic acid salt of sunitinib.

BRIEF DESCRIPTION OF THE DRAWINGS

FIG. 1 depicts the X-ray powder diffraction (XRPD) pattern of crystalline Form I of an ascorbic acid salt of sunitinib.

FIG. 1A provides the table of values for the XRPD pattern depicted in FIG. 1.

FIG. 2 depicts the differential scanning calorimetry (DSC) pattern of crystalline Form I of an ascorbic acid salt of sunitinib.

DETAILED DESCRIPTION OF THE INVENTION

The term "about", as used herein, refers to any value which lies within the range defined by a variation of up to ±10% of the value.

The term "an ascorbic acid salt of sunitinib", as used herein, refers to sunitinib ascorbate.

A first aspect of the present invention provides an ascorbic acid salt of sunitinib.

In an embodiment of the first aspect, the ascorbic acid salt of sunitinib is crystalline.

A second aspect of the present invention provides a crystalline Form I of an ascorbic acid salt of sunitinib.

In an embodiment of the second aspect, the crystalline Form I of an ascorbic acid salt of sunitinib is characterized by XRPD peaks at interplanar spacing (d) values at about 8.00, 7.84, 6.08, 3.99, 3.79, and 3.33 (Å). The XRPD further comprises interplanar spacing (d) values at about 15.97, 11.47, 10.53, 9.65, 8.00, 7.84, 6.70, 6.08, 5.68, 5.31, 4.80, 4.52, 3.99, 3.79, 3.33, 2.82, and 2.42 (Å). The crystalline Form I of an ascorbic acid salt of sunitinib is further characterized by an XRPD pattern substantially as depicted in FIG. 1.

In another embodiment of the second aspect, the crystalline Form I of an ascorbic acid salt of sunitinib is further characterized by a differential scanning calorimetry (DSC) thermogram substantially as depicted in FIG. 2. The crystalline Form I of an ascorbic acid salt of sunitinib has characteristic DSC endothermic peaks at about 90.78° C., 145.14° C., 155.95° C., 196.09° C., and about 211.33° C.

A third aspect of the present invention provides a process for the preparation of an ascorbic acid salt of sunitinib, comprising:

a) treating sunitinib with an ascorbic acid; and b) isolating an ascorbic acid salt of sunitinib from the reaction mixture of step a).

In an embodiment of the third aspect, the ascorbic acid salt of sunitinib is crystalline Form I, which is characterized by an XRPD or a DSC as depicted in FIG. 1 and FIG. 2, respectively.

The crystalline Form I of an ascorbic acid salt of sunitinib is characterized by XRPD peaks at interplanar spacing (d) values at about 8.00, 7.84, 6.08, 3.99, 3.79, and 3.33 (Å). The XRPD further comprises interplanar spacing (d) values at about 15.97, 11.47, 10.53, 9.65, 8.00, 7.84, 6.70, 6.08, 5.68, 5.31, 4.80, 4.52, 3.99, 3.79, 3.33, 2.82, and 2.42 (Å). The crystalline Form I of an ascorbic acid salt of sunitinib is further characterized by an XRPD pattern as depicted in FIG. 1.

The crystalline Form I of an ascorbic acid salt of sunitinib is also characterized by a DSC thermogram substantially as depicted in FIG. 2. The crystalline Form I of an ascorbic acid salt of sunitinib has characteristic DSC endothermic peaks at about 90.78° C., 145.14° C., 155.95° C., 196.09° C., and about 211.33° C.

Sunitinib may be prepared by any of the methods known in the art, such as those described in U.S. Pat. Nos. 7,125,905 and 6,573,293. The sunitinib used in step a) may be solid or in the form of a solution carried forward from the previous step(s).

The ascorbic acid used for the preparation of an ascorbic acid salt of sunitinib may be an L-ascorbic acid, a D-ascorbic acid, or mixtures thereof. The preferred ascorbic acid is an L-ascorbic acid.

In another embodiment of the third aspect, the treatment of sunitinib with an ascorbic acid is carried out in the presence of an organic solvent.

Suitable organic solvents may be selected from the group consisting of water, ethers, alcohols, ketones, hydrocarbons, esters, halogenated hydrocarbons, and mixtures thereof. Examples of ether solvents include methyl t-butyl ether, tetrahydrofuran, or diethyl ether. Examples of alcohol solvents include methanol, ethanol, or n-butanol. Examples of ketone solvents include acetone or methyl ethyl ketone. Examples of hydrocarbon solvents include pentane, hexane, or heptane. Examples of ester solvents include ethyl acetate, butyl acetate, or isopropyl acetate. An example of a halogenated hydrocarbon is dichloromethane. Preferably, the organic solvent used is methanol, methyl t-butyl ether, or mixtures thereof.

The isolation of the ascorbic acid salt of sunitinib from the reaction mixture of step a) is performed by filtration, cooling, evaporation, decantation, distillation, vacuum drying, or combinations thereof.

A fourth aspect of the present invention provides a pharmaceutical composition comprising an ascorbic acid salt of sunitinib and a pharmaceutically acceptable carrier.

A fifth aspect of the present invention provides a method of treating or preventing a protein kinase related disorder, which includes administering to a patient in need thereof a therapeutically effective amount of an ascorbic acid salt of sunitinib.

The XRPD of the samples were determined by using a PANalytical® X"Pert Pro X-Ray Powder Diffractometer in the range 3-40 degree 2 theta and under tube voltage and current of 45 Kv and 40 mA respectively. Copper radiation of wavelength 1.54 angstrom and an X'Celerator® detector were used.

The DSC of the sample was recorded using a Mettler Toledo® DSC 821 instrument.

While the present invention has been described in terms of its specific embodiments, certain modifications and equivalents will be apparent to those skilled in the art and are intended to be included within the scope of the present invention.

EXAMPLE

Preparation of an Ascorbic Acid Salt of Sunitinib:

Sunitinib (20 g) and L-ascorbic acid (13.25 g) were added to methanol (100 mL) at 20° C. to 30° C. The solution was heated to 50° C. to 55° C. for 1 hour, then cooled to 20° C. to 30° C. Methyl t-butyl ether (100 mL) was added to the solution over 30 minutes and the reaction mixture was stirred for 20 hours. The solid obtained was filtered, washed with methanol:methyl t-butyl ether (40 mL; 1:1 ratio), and dried under vacuum at 50° C. to 55° C. for 6 hours to obtain the title compound.

Yield: 20.2 g

Chromatographic Purity: 99.29%

XRPD: As depicted in FIG. 1

DSC: As depicted in FIG. 2.

The invention claimed is:

1. A crystalline Form I of an ascorbic acid salt of sunitinib characterized by an XRPD pattern substantially as depicted in FIG. 1.

2. The crystalline Form I of an ascorbic acid salt of sunitinib according to claim 1, characterized by XRPD peaks at interplanar spacing (d) values at about 8.00, 7.84, 6.08, 3.99, 3.79, and 3.33 (Å).

3. The crystalline Form I of an ascorbic acid salt of sunitinib according to claim 2, further characterized by XRPD peaks at interplanar spacing (d) values at about 15.97, 11.47, 10.53, 9.65, 8.00, 7.84, 6.70, 6.08, 5.68, 5.31, 4.80, 4.52, 3.99, 3.79, 3.33, 2.82, and 2.42 (Å).

4. The crystalline Form I of an ascorbic acid salt of sunitinib according to claim 1, characterized by a DSC thermogram substantially as depicted in FIG. 2.

5. The crystalline Form I of an ascorbic acid salt of sunitinib according to claim 1, characterized by DSC endothermic peaks at about 90.78° C., 145.14° C., 155.95° C., 196.09° C., and about 211.33° C.

6. A process for the preparation of the crystalline Form I of claim 1 comprising:
a) treating sunitinib with an ascorbic acid; and
b) isolating the crystalline Form I from the reaction mixture of step a).

7. The process according to claim 6, wherein the ascorbic acid used for the preparation of the salt of sunitinib is L-ascorbic acid, D-ascorbic acid, or mixtures thereof.

8. The process according to claim 7, wherein the ascorbic acid used for the preparation of the salt of sunitinib is L-ascorbic acid.

9. The process according to claim 6, wherein the treatment of sunitinib with an ascorbic acid is carried out in the presence of an organic solvent selected from the group consisting of water, ethers, alcohols, ketones, hydrocarbons, esters, halogenated hydrocarbons, and mixtures thereof.

10. The process according to claim 9, wherein the ether solvents are selected from the group consisting of methyl tertiary butyl ether, tetrahydrofuran, or diethyl ether.

11. The process according to claim 9, wherein the alcohol solvents are selected from the group consisting of methanol, ethanol, or n-butanol.

12. The process according to claim 9, wherein the ketone solvents are selected from the group consisting of acetone or methyl ethyl ketone.

13. The process according to claim 9, wherein the hydrocarbon solvents are selected from the group consisting of pentane, hexane, or heptane.

14. The process according to claim 9, wherein the ester solvents are selected from the group consisting of ethyl acetate, butyl acetate, or isopropyl acetate.

15. The process according to claim 9, wherein the halogenated hydrocarbon is dichloromethane.

16. The process according to claim 9, wherein the organic solvent is methanol or methyl tertiary butyl ether.

17. A pharmaceutical composition comprising the crystalline Form I of claim 1 and a pharmaceutically acceptable carrier.

18. A method of treating or preventing a protein kinase related disorder, comprising administering to a patient in need thereof a therapeutically effective amount of the crystalline Form I of claim 1.

* * * * *